United States Patent [19]

Evans et al.

[11] Patent Number: 4,814,276

[45] Date of Patent: Mar. 21, 1989

[54] SELECTIVE MEDIUM FOR GROWTH OF NEISSERIA

[75] Inventors: George L. Evans, Cockeysville; Deborah L. De Vaux Kopyta, Hampstead, both of Md.

[73] Assignee: Becton, Dickinson and Company, Franklin Lakes, N.J.

[21] Appl. No.: 56,029

[22] Filed: Jun. 1, 1987

Related U.S. Application Data

[63] Continuation-in-part of Ser. No. 855,554, Apr. 25, 1986, abandoned.

[51] Int. Cl.$^4$ ............................ C12N 1/20; C12Q 1/04; C12Q 1/12; C12R 1/36
[52] U.S. Cl. ................................... 435/253.6; 435/34; 435/37; 435/871; 435/252.1; 514/43
[58] Field of Search .................. 435/34, 37, 253, 871; 514/43

[56] References Cited

PUBLICATIONS

Strickett, M. G. et al., Pathology, vol. 15, pp. 457–462.
Symington, D. A. "Improved Transport System for *Neisseria Gonorrhoeae* in Clinical Specimens" *J. Clin. Micro.* vol. 2, pp. 498–503 (1975).
Thayer, et al. "Improved Medium Selective for Cultivation of *N. Gonorrhoeae* and *N. Meningitidis*" Public Health Reports vol. 81, pp. 559–562 (1966).
Young, H. "Cultural Diagnosis of Gonorrhoea with Modified New York City (MNYC) Medium" *Brit. J. Vener. Dis.* vol. 54, pp. 36–40 (1978).
Anstey, et al. "Laboratory and Clinical Evaluation of Modified New York City Medium, (Henderson Formulation) for the Isolation of *Neisseria Gonorrhoeae*." J. Clin. Micro., vol. 20, pp. 905–908 (1984).
Bonin, et al. "Isolation of *Neisseria Gonorrhoeae* on Selective and Nonselective Media in a Sexually Transmitted Disease Clinic" J. Clin. vol. 19, pp. 218–392 (1984).
Biological Abstracts, vol. 66, No. 4, 1978, p. 2182, Abstract No. 22286.
Biological Abstracts, vol. 73, No. 2, 1982, p. 1127, Abstract No. 10963.
Chemical Abstracts, vol. 103, No. 23, Dec. 9, 1985, p. 397, Abstract No. 193055y.
Young, H. "Identification and Penicillinase Testing of *Neisseria Gonorrhoeae* from Primary Isolation Cultures on Modified New York City Medium" *J. Clin. Micro.* vol. 7, pp. 247–250 (1978).
"Faur, et al. Recovery of Vancomycin Sensitive *Neisseria Gonorrhoeae* on Modified NYC Medium" Program of the 88th Annual Meeting of Amer. Soc. Micro. C-29 p. 336 (1988).
Reyn, et al. "Comparison of a Selective and a Non-Selective Medium in the Diagnosis of Gonorrhoeae to Ascertain the Sensitivity of *Neisseria Gonorrhoeae* to Vancomycin" Brit. J. Vener. Dis. vol. 48, pp. 363–368 (1972).
Robinson, et al. "Use of Vancomycin, Colistimethate, Nystatin Medium to Transport Gonococcal Specimens" *Public Health Reports* vol. 85, pp. 390–392 (1970).
Svarva, et al. "Comparison of Two Selective Media in the Cultural Diagnosis of Gonorrhoeae" *Acta. Path. Micro. Scan. Sect. B.* vol. 87, pp. 391–392 (1979).
Odegaard, et al. "Lincomycin In Selective Medium for the Isolation of *Neisseria Gonorrhoeae*" Acta. Path. Micro. Scand. Section B. vol. 83, pp. 301–304 (1975).
Philips, et al. "Diagnosis of Gonorrhoeae by Culture on a Selective Medium Containing Vancomycin, Colistin, Nystatin and Trimethoprim (VCNT)" *Brit. J. Vener. Dis.* vol. 48, pp. 287–292 (1972).
Potuznik, et al. "Selective Medium with Lincomycin and Colistin for the Isolation of *Pathogenic Neisseriae*" *J. Hyg. Cpid, Micro.* vol. 11, p. 127 (1967).
Kraus, et al. "Interference of *Neisseria Gonorrhoeae* Growth by Other Bacterial Species" *J. Clin. Micro.* vol. 4, pp. 288–295 (1976).
Martin, et al. "*Neisseria Gonorrhoeae* and *Neisseria Meningitidis* Sensitivity to Spectinomycin, Lincomycin, and Penicillin G" *Agents Chemo,* pp. 437–439 (1965).
Martin, et al. "Primary Isolation of *N. Gonorrhoeae* With a New Commercial Medium" Public Health Reports vol. 82, pp. 361–363 (1967).
Martin, et al. "New System for Cultivation of *Neisseria Gonorrhoeae* " *Appl. Micro.* vol 27, pp. 802–805 (1967).
Martin, et al. "A Biological Environmental Chamber for the Culture of *neisseria Gonorrhoeae*\*" *J. Am. Vener. Dis. Assoc.* vol. 2, pp. 28–30 (1975).
Mirret, et al. "*Neisseria Gonorrhoeae* Strains Inhibited by Vancomycin in Selective Media and Correlation with Auxotype" *J. Clin. Micro.* vol. 14, pp. 94–99 (1981).
Fauer, et al. "Correspondence to the Editor Re:Lincomycin Versus Vancomycin in New York City (NYC) Medium for the Cultural Diagnosis of Gonorrhoeae" *Brit. J. Vener. Dis. vol. 58, pp. 66 (1966).*
Granato, et al. "Comparison of Modified New York City Medium with Martin-Lewis Medium for Recovery of *Neisseria Gonorrhoeae* from Clinical Specimens" J. Clin. Mirco. vol. 12, pp. 748–752 (1980).
Hipp, et al. "Inhibition of *Neisseria Gonorrhoeae* by a Factor Produced by *Candida Albicans*" Appl. Micro. vol. 27, pp. 192–196 (1974).

(List continued on next page.)

*Primary Examiner*—Thomas G. Wiseman
*Assistant Examiner*—Joan Ellis
*Attorney, Agent, or Firm*—Mary M. Allen

[57] ABSTRACT

A nutrient growth medium which is highly selective for pathogenic Neisseria is provided. The nutrient growth medium includes an antibiotic agent which is a combination of vancomycin and lincomycin. The combination of lincomycin and vancomycin allows the use of lower concentrations of vancomycin than are generally employed in culture media used for the selective isolation of pathogenic Neisseria species.

8 Claims, No Drawings

OTHER PUBLICATIONS

Brorson, et al. "Vancomycin-Sensitive Strains of *Neisseria Gonorrhoeae* A Problem for the Diagnostic Laboratory" *Brit. J. Vener. Dis.* vol. 49, pp. 452–453 (1973).

Cross, et al. "VCN-Inhibited Strains of *Neisseria Gonorrhoeae*" *HSMHA Health Reports.* vol. 86, pp. 990–992 (1971).

Faur, et al. "The Sensitivity of Vancomycin and Lincomycin in NYC Medium for the Recovery of *N. Gonorrhoeae* from Clinical Specimens" *Health Lab. Sci.* vol. 15, pp. 22–27 (1978).

SELECTIVE MEDIUM FOR GROWTH OF NEISSERIA

The present application is a Continuation-in-part of U.S. patent application Ser. No. 855,554 filed Apr. 25, 1986 now abandoned.

The present invention relates to rapid detection and presumptive identification of Neiserria species, particularly Neisseria gonorrhoeae, by means of a selective agar medium.

BACKGROUND OF THE INVENTION

The need for developing means for rapid and accurate cultivation and primary isolation of pathogenic Neisseria species, such as *N. gonorrhoeae* and *N. meningitidis*, has greatly increased in recent years. A substantial amount of research and development has occurred in an attempt to provide a growth medium for Neisseria which is selective for Neisseria and which inhibits the growth of other microorganisms. A principal problem occurs in that antibiotics which are associated with selective media for Neisseria inhibit the growth of antibiotic-sensitive Neisseria species, such as *N. gonorrhoeae*. Also, antibiotics, such as vancomycin, which are associated with selective media for *N. gonorrhoeae*, while prohibiting growth of certain sensitive *N. gonorrhoeae*, also do not act to inhibit growth of other particular gram negative species, such as Capnocytophaga.

The high level of activity and concern for the development of an improved selective medium for *N. gonorrhoeae* is amply demonstrated by the following list of references which are all, in some way, associated with the development of selective media for the isolation and growth of *N. gonorrhoeae*:

Anstey, R. J., J. Gun-Munro, R. P. Rennie, J. H. Thornley, D. G. Schaus, R, Lannigan, Z. Hussain, and R. S. Maharaja. 1984. Laboratory and clincal evaluation of modified New York City medium (Henderson formulation) for the isolation of *Neisseria gonorrhoeae*. J. Clin. Microbiol.20:905-908.

Berger, U. 1966. A new selective medium for *Neisseria meningitidis* and *Neisseria gonorrhoeae*. A. Med. Mikrobiol. U. Immunol. 152: 169-172.

Bonin, P., T. Tanino, and H. H. Handsfield. 1984. Isolation of *Neisseria gonorrhoeae* on selective and nonselective media in a sexually transmitted disease clinic. J. Clin. Microbiol. 19: 218-392.

Brorson, J., I. Holmberg, B. Nygren, and S. Seeberg. 1973. Vancomycin-sensitive strains of *Neisseria gonorrhoeae*: a problem for the diagnostic laboratory. Brit. J. Vener. Dis. 49:452-453.

Cross, R. C., M. B. Hoger, R. Neibaur, B. Pasternack, and F. J. Brady. 1971. VCN-inhibited strains of *Neisseria gonorrhoeae*. HSMHA Health Reports. 86:990-992.

Faur, Y. C., M. H. Weisburd, and M. E. Wilson, 1978. The selectivity of vancomycin and lincomycin in NYC medium for the recovery of *N. gonorrhoeae* from clinical specimens. Health Lab. Sci. 15: 22-27.

Faur, Y. C., and M. E. Wilson. 1982. Correspondence to the editor re: lincomycin versus vancomycin in New York City (NYC) medium for the cultural diagnosis of gonorrhoeae. Brit. J. Vener. Dis. 58: 66.

Granato, P. A., J. L. Paepke, and L. B. Weiner. 1980. Comparison of modified New York City medium with Martin-Lewis medium for recovery of *Neisseria gonorrhoeae* from clinical specimens. J. Clin. Microbiol. 12: 748-754.

Hipp, S. S., W. D. Lawton, N. C. Chen, and H. A. Gaffar, 1974. Inhibition of *Neisseria gonorrhoeae* by a factor produced by *Candida albicans*. Appl. Microbiol. 27: 192-196.

Kraus, S. J., R. C. Geller, G. H. Perkins, and D. L. Rhoden. 1976. Interference of *Neisseria gonorrhoeae* growth by other bacterial species. J. Clin. Microbiol. 4: 228-295.

Martin, J. E., Jr., S. B. Samuels, W. L. Peacock, Jr., and J. D. Thayer. 1964. *Neisseria gonorrhoeae* and *Neisseria meningitidis* sensitivity to spectinomycin, lincomycin, and penicillin G. Antimicrob. Agents Chemo. p. 437-439.

Martin, J. E., Jr., T. E. Billings, J. Hackney J. Thayer. 1967. Primary isolation of *N. gonorrhoeae* with a new commerical medium. Public Health Reports. 82: 361-363.

Martin, J. E., J. Armstrong, and P. B. Smith. 1971. New system for cultivation of *Neisseria gonorrhoeae*. Appl. Microbiol. 27: 802-805.

Martin, J. E., Jr., and R. Jackson, 1975. A biological enviromental chamber for the culture *Neisseria gonorrhoeae*. J. Am. Vener. Dis. Assoc. 2: 28-30.

Mirret, S., L. Reller, and J. Knapp. 1981. *Neisseria gonorrhoeae* strains inhibited by vancomycin in selective media and correlation with auxotype. J. Clin. Microbiol. 14: 94-99.

Odegaard, K., O. Solberg, J. Ling, G. Myhre, and B. Nyland. 1975. Lincomycin in selective medium for the isolation of *Neisseria gonorrhoeae*. Acta. path. microbiol. scand. Sect. B. 83: 301-304.

Phillips, I., D. Humphrey, A. Middleton, and C. S. Nicol. 1972. Diagnosis of gonorrhoeae by culture on a selective medium containing vancomycin, colistin, nystatin, and trimethoprim (VCNT). Brit. J. Vener. Dis. 48: 287-292.

Potuznik, V., O. Hausner. 1967. Selective medium with lincomycin and colistin for the isolation of pathogenic Neisseria. J. Hygiene, Cpid., Micro. 11: 127.

Reyn, A. and M. Bentzon. 1972. Comparison of a selective and nonselective medium in the diagnosis of gonorrhoeae to ascertain the sensitivity of *Neisseria gonorrhoeae* to vancomycin. Brit. J. Vener. Dis. 48: 363-368.

Robinson, M., C. Hicks, and G. Davidson, 1970. Use of vancomycin, colistimethate, nystatin medium to transport gonococcal specimens. Public Health Reports. 85: 390-392.

Svarva, P., and J. Maeland. 1979. Comparison of two selective media in the cultural diagnosis of gonorrhoeae. Acta. Path. microbiol scanda. Sect. B., 87: 391-391.

Symington, D. A. 1975. Improved transport system for *Neisseria gonorrhoeae* in clinical specimens. J. Clin. Microbiol. 2: 498-503.

Thayer, J. D., and J. E. Martin, Jr. 1966. Improved medium selective for cultivation of *N. gonorrhoeae* and *N. meningitidis*. Public Health Reports. 81: 559-562.

Young, H. 1978. Cultural diagnosis of gonorrhoeae with modified New York City (MNYC) medium. Brit. J. Vener. dis. 54: 36-40.

Young, H. 1978. Identification and penicillinase testing of *Neisseria gonorrhoeae* from primary isolation cultures on modified New York City medium. J. Clin. Microbiol. 7: 247-250.

While the above list of prior art references amply demonstrate the need for an improved growth media for the isolation and detection of Neisseria species, such as *N. gonorrhoeae*, none of the references set forth herein above describe the present invention which is directed to the provision of a highly selective culture medium for *N. gonorrhoeae* and *N meningitidis*.

SUMMARY OF THE INVENTION

In general, in accordance with the invention, there is provided a nutrient growth medium which is highly selective for pathogenic Neisseria. The nutrient growth medium includes an antibiotic agent which is a combination of vancomycin and lincomycin. The vancomycin is used at levels substantially lower than heretofore reported for the use of vancomycin in culture media used for the selective culturing of pathogenic Neisseria species, such as *N. gonorrhoeae*. The use of lower levels of vancomycin permits the growth of vancomycin-sensitive Neisseria species. The lincomycin is used at a sufficient level to inhibit the growth of other gram negative species, such as Capnocytophaga and gram positive species such as staphylococci, which have been a problem in the use of other selective media for Neisseria which have used reduced levels of vancomycin. Also present in the selective growth media of the present invention are a diaminopyrimidine, such as trimethoprim, for inhibition of Proteus species, an antifungal agent and a polymixin.

Accordingly, it is a primary object of the present invention to provide a growth medium for improved culturing of pathogenic Neisseria.

It is another object of the present invention to provide a medium and method for culturing pathogenic Neisseria which permits primary isolation of pathogenic species of the Neisseria genus.

It is a further object of the present invention to provide a composition which is selective for the growth of pathogenic Neisseria but which inhibits growth of other bacteria and fungi.

DESCRIPTION OF THE PREFERRED EMBODIMENTS

The components of the selective culture medium of the present invention include a nutrient agar base, a source of hemoglobin, and enrichment agent and selective agents.

The preferred nutrient agar base is GC Agar base which has the following composition in grams per liter of completed medium:

| | |
|---|---|
| Pancreatic digest of casein | 7.5 g |
| Peptic digest of animal tissue | 7.5 |
| Corn starch | 1.0 |
| Dipotassium phosphate | 4.0 |
| Monopotassium phosphate | 1.0 |
| Sodium chloride | 5.0 |
| Agar | 10.0 |

The preferred source of hemoglobin is dried bovine hemoglobin in a concentration of approximately 10.0 g/L.

The preferred enrichment agent is supplied by the BBL Microbiology Systems Division of Becton-Dickinson and Company under the tradename IsoVitaleX-®Enrichment. The final concentration of IsoVitaleX Enrichment used in the nutrient agar base is 10.0 ml per liter. The composition per liter of IsoVitaleX Enrichment is:

| | |
|---|---|
| Vitamin B12 | 0.01 g |
| L—Glutamine | 10.0 |
| Adenine | 1.0 |
| Guanine Hydrochloride | 0.03 |
| p-Aminobenzoic Acid | 0.013 |
| Nicotinamide Adenine Dinucleotide | 0.25 |
| Thiamine Pyrophosphate | 0.1 |
| Ferric Nitrate | 0.02 |
| Thiamine Hydrochloride | 0.003 |
| L—Cysteine Hydrochloride | 25.9 |
| L—Cystine | 1.1 |
| Dextrose | 100.0 |

The inhibitor of the invention includes an antibiotic agent that inhibits gram-positive bacteria, especially staphylococci and is active against Capnocytophaga species, an agent active against gram-negative bacteria, an agent that inhibits Proteus species, and an antifungal agent.

The preferred antibiotic agent for inhibition of gram-positive bacteria and Capnocytophaga is a combination of vancomycin and lincomycin which allows the growth of even vancomycin-sensitive *Neisseria gonorrhoeae* while completely inhibiting the growth of Capnocytophaga species and Staphylococci including vancomycin-resistant strains. The amount of vancomycin is from about 1.0 to 4.0 micrograms per milliliter of growth medium and the lincomycin from about 0.5 to about 3.0 micrograms per milliliter of growth medium.

Lincomycin is known for use as a replacement for vancomycin in a selective medium for the isolation of *N. gonorrhoeae*, K. Odegaard et al., "Lincomycin In Selective Medium For The Isolation of *Neisseria Gonorrhoeae*", Acta. path. microbiol. scand. Sect. B, 83: 301–304, 1975. However, there is no suggestion in this reference or any other reference that the inventors are aware of that lincomycin can be combined with vancomycin to provide an improved antibiotic agent in a selective medium for the isolation of Neisseria species.

Lincomycin is also known for use as an anti-bacterial agent against the majority of strains of Bacteroides. However, it is known that lincomycin is ineffective against meningococci and gonococci. Clindamycin is a chlorinate derivative of lincomycin and is known to be more active in vivo than lincomycin. However, clindamycin cannot replace lincomycin in the selective growth medium of the present invention since it is active against Neisseria species.

The agent active against Proteus species is a diaminopyrimidine. The preferred Proteus active agent is trimethoprim or trimethoprim lactate in a concentration of 2 to about 8 micrograms per milliliter.

The anti-fungal agent is preferably selected from the group consisting of nystatin, anisomycin, miconazole and amphotericin B. The preferred anti-fungal agent is amphotericin B and is present in the selective growth medium of the present invention at a level of from about 1 to about 5 micrograms per milliliter of growth medium. The agent active against gram-negative bacteria is preferably a polymyxin which is preferably present in the growth medium at a level from about 5 to about 10 micrograms per milliliter of growth medium. The polymyxin is preferably colistin sulfate.

The following examples are provided to further illustrate the present invention. The scope of the invention is not, however, meant to be limited to the specific details of the examples.

Example 1

To prepare one liter of the inhibitor of the present invention, each of the following is dissolved in about 750 ml of purified water: (1) 200 milligrams vancomycin, (2) 750 milligrams colistin sulfate or colistin sodium methane sulfonate, (3) 150 milligrams amphotericin B (which is first dissolved in a small amount of 1 N.NaOH), (4) 100 milligrams lincomycin, and (5) 500 milligrams trimethoprim base or trimethoprim lactate. Sufficient purified water is added to the inhibitor solution to bring the volume to 1 liter. The solution is then sterilized by filtration through a 0.22 micron filter. Ten milliliters of this solution is used to prepare one liter of the complete medium.

A similar inhibitor solution is prepared wherein the lincomycin is deleted from the formula, the vancomycin is adjusted to 300 milligram per liter, and the amphotericin B is replaced by 1,250,000 units per liter of nystatin.

A modified Thayer-Martin medium is made by combining GC Agar Base, hemoglobin, IsoVitaleX Enrichment and the above described inhibitor that does not contain lincomycin. A similar preparation is made using the inhibitor of the present invention as described above containing lincomycin. The two growth media have the composition per liter as indicated hereinbelow:

| Ingredient | Growth Medium of the Invention (Medium A) | Modified Thayer-Martin Medium (Medium B) |
| --- | --- | --- |
| GC Agar Base | 36.0 g | 36.0 g |
| Hemoglobin | 10.0 g | 10.0 g |
| IsoVitaleX Enrichment | 10.0 ml | 10.0 ml |
| Vancomycin | 2.0 mg | 3.0 mg |
| Lincomycin | 1.0 mg | — |
| Colistin Sulfate | 7.5 mg | 7.5 mg |
| Trimethoprim | 5.0 mg | 5.0 mg |
| Amphotericin B | 1.5 mg | — |
| Nystatin | — | 12,500 units |

After the growth media are prepared, they are dispensed into 100 mm petri dishes according to standard bacteriological practive. After the medium has gelled, the dishes are placed in a suitable container and are stored at 2° to 8° C. until ready for use. The plates may be stored at this temperature for up to 14 weeks.

Both stock cultures and clinical specimens were used to evaluate the performance of the two media. The cultures were inoculated according to standard bacteriologic practices; growth or inhibition was scored after appropriate incubation in a CO2-enriched enviroment.

The ATCC ® cultures used included *Neisseria gonorrhoeae* 43069, 43070, 35201, *N.* neningitidis 13090, *Candida albicans* 60193, *Neisseria sicca* 9913, *Proteus mirabilis* 43071, *Staphyloccocus epidermidis* 12228, and *Capnocytophaga ochracea* 33595. Six clinical strains of vencomycin-susceptible *N. gonorrhoeae* from patient specimens were tested as well as six Capnocytophaga species, isolated from oropharyngeal cultures, and one vancomycin-resistant Staphylococcus.

| Parameters | Results Observed on Medium | |
| --- | --- | --- |
| | A | B |
| Recovery of pathogenic Neisseria | + + + + | + + + + |
| Recovery of vancomycin-susceptible *N. gonorrhoeae* | + + + | + + |
| Inhibition of Yeasts | + + + + | + + + |
| Inhibition of Capnocytophaga | + + + + | — |
| Inhibition of vancomycin-resistant *S. epidermidis* | + + + + | + |
| Inhibition of other normal flora | + + + + | + + + + |

+ + + + Excellent
+ + + Good
+ + Fair
Media Code
A = Medium of the present invention
B = Modified Thayer - Martin Medium The results, as set forth in the above table, illustrate the surprising improvement of the selective agent of the present invention over selective agents known in the prior art.

What is claimed is:

1. A culture medium for the selective growth of pathogenic Neisseria which comprises:
    sources of carbon, nitrogen and nutrients sufficient to support growth of pathogenic Neisseria, and
    an antibiotic composition including a mixture of vancomycin and lincomycin.

2. A culture medium in accordance with claim 1 wherein said vancomycin is present at a level of from about 1 to about 4 micrograms per milliliter of culture medium and said lincomycin is present at a level of from about 0.5 to about 3 micrograms per milliliter of culture medium.

3. A culture medium in accordance with claim 1 which includes a diaminopyrimidine.

4. A culture medium in accordance with claim 3 wherein said diaminopyrimidine is present at a level of from about 2 to about 8 micrograms per milliliter of culture medium.

5. A culture medium in accordance with claim 1 which includes an antifungal agent selected from the group consisting of nyotatin, anisomycin, miconazole and amphotericin B.

6. A culture medium in accordance with claim 5 wherein said antifungal agent is present at a level sufficient to inhibit growth of yeasts.

7. A culture medium in accordance with claim 1 which includes a polymyxin.

8. A culture medium in accordance with claim 7 wherein said polymyxin is present at a level of from about 5 to about 10 micrograms per milliliter of growth medium.

* * * * *